United States Patent [19]
Giba et al.

[11] Patent Number: 6,126,654
[45] Date of Patent: Oct. 3, 2000

[54] METHOD OF FORMING REVASCULARIZATION CHANNELS IN MYOCARDIUM USING A STEERABLE CATHETER

[75] Inventors: Jeffrey Giba, Sunnyvale; Michael Horzewski, Santa Clara, both of Calif.; James Edward Wilson, Bound Brook, N.J.

[73] Assignee: Eclipse Surgical Technologies, Inc., Sunnyvale, Calif.

[21] Appl. No.: 09/256,126

[22] Filed: Feb. 24, 1999

Related U.S. Application Data

[63] Continuation of application No. 08/833,352, Apr. 4, 1997, Pat. No. 5,876,373.

[51] Int. Cl.⁷ .................................................. A61B 17/36
[52] U.S. Cl. .............................. 606/15; 604/95; 604/511; 607/122
[58] Field of Search .............................. 604/95, 264, 523, 604/530, 500, 511; 600/139, 146–151; 606/15, 16; 607/122

[56] References Cited

U.S. PATENT DOCUMENTS

| | | | |
|---|---|---|---|
| 3,890,977 | 6/1975 | Wilson | 128/418 |
| 4,658,817 | 4/1987 | Hardy | 128/303 |

(List continued on next page.)

FOREIGN PATENT DOCUMENTS

| | | |
|---|---|---|
| 0 515 867 A2 | 12/1992 | European Pat. Off. . |
| WO 6/35469 A1 | 11/1996 | WIPO . |

OTHER PUBLICATIONS

Deckelman, L.I., "Cardiovascular Applications of Laser Technology," Lasers in Surgery and Medciine. 15:315–341 (1994).

Frazier, O.H., "Myocardial Revascularization with Lazer—Preliminary Findings," Circulation, 1995; 92[suppl. II]: II-58–II-65.

Duerig et al, Structure and Properties of Ti–NI Alloys: Nitinol Devices & Components, In press, Titanium Handbook, AS (1994).

*Primary Examiner*—Corrine McDermott
*Attorney, Agent, or Firm*—Janet Kaiser Castaneda

[57] ABSTRACT

An elongated steerable catheter for placement within a heart chamber, organ aperture or other body opening and having at least one center tube with hollow passageway for guiding a laser delivery means or other functional device to selected surfaces of a heart chamber, organ aperture or other body cavity for laser or other treatment thereon, particularly adapted for laser-assisted percutaneous transmyocardial revascularization (TMR), is disclosed herein. The steerable catheter has a handle portion at its proximal end and a controllably deflectable end portion at its distal end. The elongated center tube has a distal end, in the region where a curvature is to be formed, and a shim anchor sleeve is slidably disposed over the center tube. The shim anchor sleeve is attached to the inside wall of the outer jacket and coupled to the distal end of the center tube with a bendable shim member which extends between the distal tip of the steerable catheter and the sleeve over the center tube. Opposite the shim is a guide for a pull cable, the pull cable attached to the distal end of the steerable catheter and extending through the guide to the handle. Thus, the shim is maintained radially opposite the pull cable with the center tube in between. An outer jacket has, in a preferred embodiment, distinct sections of different stiffness or durometer. A distal, more flexible portion is coupled to a proximal, stiffer portion. The shim anchor sleeve is positioned at or near the junction of two portions of the outer jacket. Thus, the center tube moves freely through the shim anchor sleeve. Adjacent the handle, the outer jacket terminates at the catheter base. The pull cable extends past the catheter base, through a deflection housing tube, and terminates in a cable stop. Rotation of a deflection knob threadably mounted onto the deflection housing tube will cause the pull cable to be pulled backward, or the outer jacket to be pushed forward, relative to each other, thereby inducing deflection of the distal end of the steerable catheter.

8 Claims, 12 Drawing Sheets

U.S. PATENT DOCUMENTS

| | | |
|---|---|---|
| 4,669,465 | 6/1987 | Moore et al. . |
| 4,790,624 | 12/1988 | Van Hoye et al. ................. 350/96.26 |
| 4,846,171 | 7/1989 | Kauphusman et al. . |
| 5,104,393 | 4/1992 | Isner ........................................... 606/15 |
| 5,114,402 | 5/1992 | McCoy ...................................... 604/95 |
| 5,190,050 | 3/1993 | Nitzsche ................................. 128/772 |
| 5,255,679 | 10/1993 | Imran ...................................... 128/642 |
| 5,318,528 | 6/1994 | Heaven et al. ............................ 604/95 |
| 5,358,479 | 10/1994 | Wilson ..................................... 604/95 |
| 5,380,316 | 1/1995 | Aita et al. ................................. 606/7 |
| 5,389,096 | 2/1995 | Aita et al. ................................. 606/15 |
| 5,397,321 | 3/1995 | Houser et al. ............................ 606/41 |
| 5,465,717 | 11/1995 | Imran et al. ............................. 128/642 |
| 5,571,085 | 11/1996 | Accisano, III ........................... 604/95 |
| 5,730,741 | 3/1998 | Horzewski et al. ....................... 606/1 |
| 5,964,757 | 10/1999 | Ponzi ....................................... 606/45 |

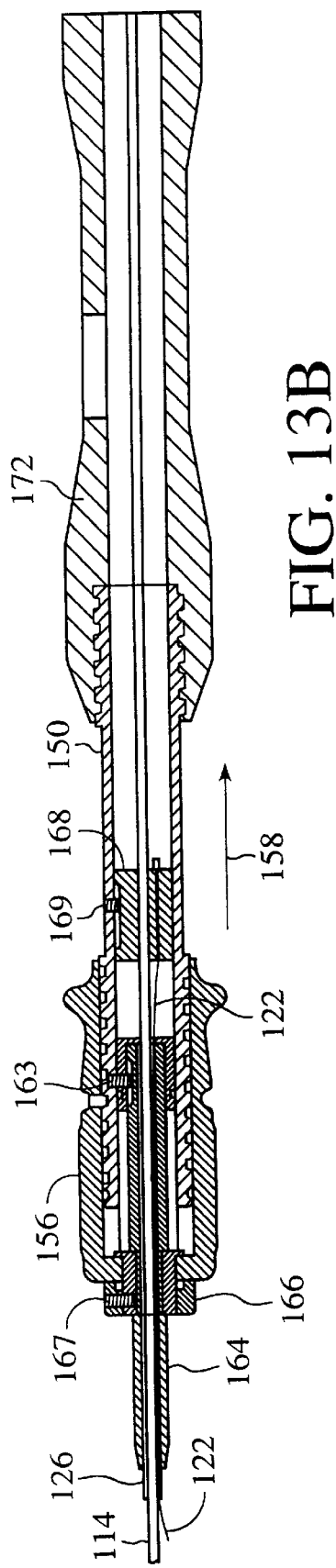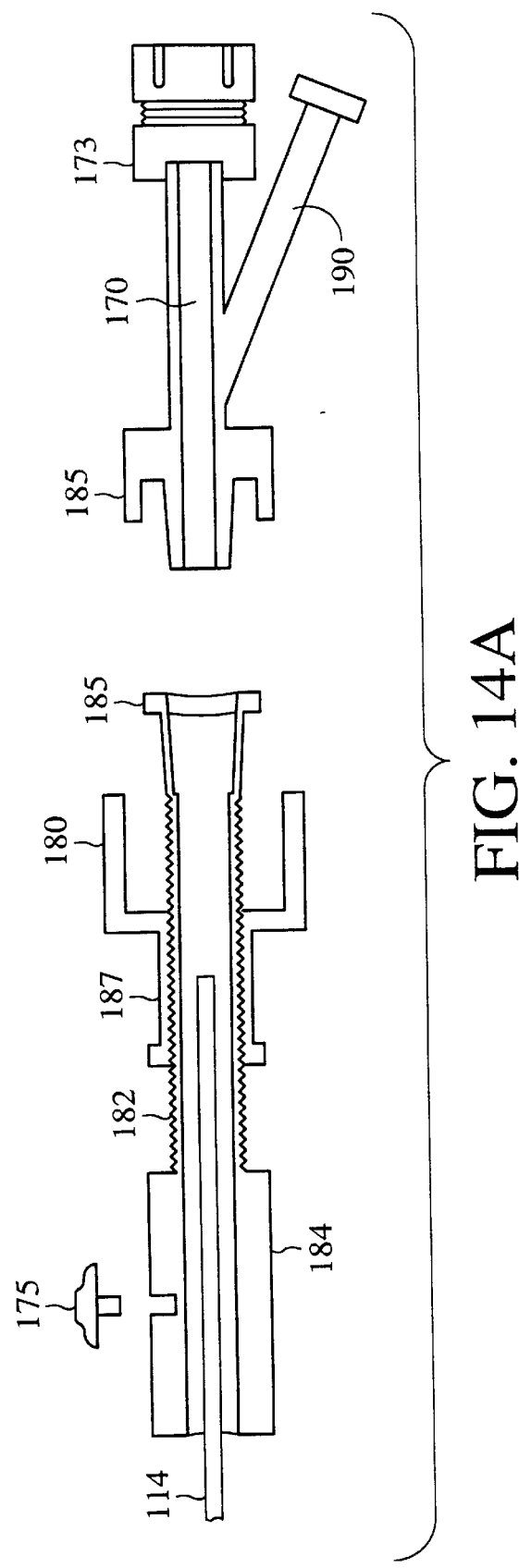

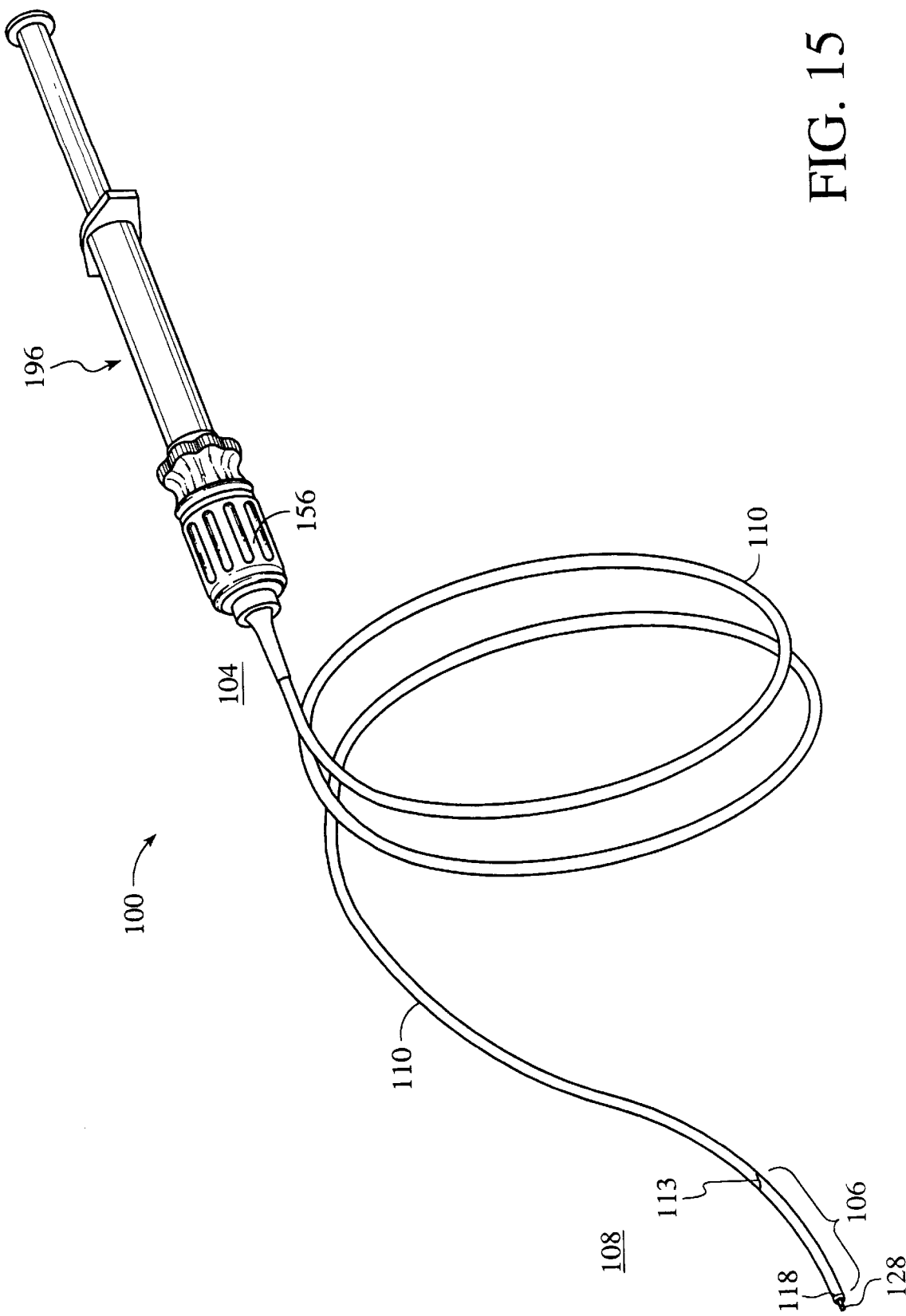

METHOD OF FORMING REVASCULARIZATION CHANNELS IN MYOCARDIUM USING A STEERABLE CATHETER

This application is a Continuation of application Ser. No. 08/833,352, filed on Apr. 4, 1997 now U.S. Pat. No. 5,876,373

FIELD OF THE INVENTION

The present invention relates generally to catheters and catheter procedures involving laser energy delivery using fiber optic and other laser delivery systems. More particularly, the invention relates to a steerable catheter and method of use, particularly adapted for laser-assisted transmyocardial revascularization (TMR). The distal tip of a central, hollow flexible center tube for guiding a laser delivery means or other functional device extendable therethrough is deflectable utilizing a semi rigid shim, the shim acted upon by a pull cable for controllably deflecting the distal tip of the steerable catheter in at least one given plane. The steerable catheter can be used in conjunction with a fiber or other laser delivery means advance mechanism, optionally using a depth control mechanism as well.

BACKGROUND OF THE INVENTION

In the treatment of heart disease, one method of improving myocardial blood supply is called transmyocardial revascularization (TMR), the creation of channels in the myocardium of the heart. The procedure using needles in a form of surgical "myocardial acupuncture" has been used clinically since the 1960s. Deckelbaum. L. I., Cardiovascular Applications of Laser Technology, *Lasers in Surgery and Medicine* 15:315–341 (1994). The technique relieves ischemia by allowing blood to pass from the ventricle through the channels either directly into other vessels communicating with the channels or into myocardial sinusoids which connect to the myocardial microcirculation.

In the reptilian heart, perfusion occurs via communicating channels between the left ventricle and the coronary arteries. Frazier, O. H., Myocardial Revascularization with Laser—Preliminary Findings, *Circulation,* 1995; 92 [suppl II]:H-58-II-65. There is evidence of these communicating channels in the developing human embryo. In the human heart, myocardial microanatomy involves the presence of myocardial sinusoids. These sinusoidal communications vary in size and structure, but represent a network of direct arterial-luminal, arterial-arterial, arterial-venous, and venous-luminal connections. This vascular mesh forms an important source of myocardial blood supply in reptiles but its role in humans is poorly understood.

Numerous surgical TMR studies have been performed, including early studies using needles to perform myocardial acupuncture, or boring, to mechanically displace and/or remove tissue. Such studies have involved surgically exposing the heart and sequentially inserting needles to form a number of channels through the epicardium, myocardium, and endocardium to allow blood from the ventricle to perfuse the channels. The early studies using needles showed that the newly created channels were subject to acute thrombosis followed by organization and fibrosis of clots resulting in channel closure. Interest in TMR using needles waned with the knowledge that such channels did not remain open. However, interest in TMR procedures has recurred with the advent of medical lasers used to create TMR channels. Histological evidence of patent, endothelium-lined tracts within laser-created channels shows that the lumen of laser channels can become hemocompatible and resists occlusion. A thin zone of charring occurs on the periphery of the laser-created channels through the well-known thermal effects of optical radiation on cardiovascular tissue. Additionally, recent histological evidence shows probable new vessel formation adjacent collagen occluded transmyocardial channels, thereby suggesting benefits from TMR with or without the formation of channels which remain patent.

Surgical TMR procedures using laser energy have been described in the prior art. U.S. Pat. No. 4,658,817 issued Apr. 21, 1987 to Hardy teaches a method and apparatus for surgical TMR using a $CO_2$ laser connected to an articulated arm having a handpiece attached thereto. The handpiece emits laser energy from a single aperture and is moved around the surface of the heart to create the desired number of channels. U.S. Pat. No. 5,380,316 issued Jan. 10, 1995 to Aita et al. purports to teach the use of a flexible lasing apparatus which is inserted into the open chest cavity in a surgical procedure. A lens at the distal end of the flexible apparatus is used to focus laser energy, and the apparatus is moved about the surface of the heart to create the desired number of channels.

The foregoing discussion relates to surgical procedures, i.e. procedures which access the heart surgically, either via open heart surgery, or perhaps by minimally invasive surgical (MIS) methods if the design and size of the distal ends of the hand pieces are suitable for use in an MIS site. However, since TMR most often involves creating channels through the endocardium into the lower left chamber of the heart, it is desirable to create TMR channels in a percutaneous procedure, i.e. by extending a catheter apparatus through the vasculature into the ventricle and creating the channels through endocardial surfaces and into myocardium. Performing such percutaneous TMR is desirable for a number of reasons. Percutaneous catheter procedures are typically less traumatic to the patient compared to surgical procedures. Adhesions between the pericardial sac and epicardium are eliminated. Percutaneous TMR with a catheter apparatus also offers an alternative solution to persons who are not candidates for surgical procedures.

Because TMR procedures generally involve creating a plurality of channels within the myocardium, performing the procedure percutaneously requires the ability to steer a catheter apparatus through the vasculature and maneuver the apparatus within the ventricle of the beating heart as rapidly as possible to create the channels without subjecting the heart to the undue stress of a lengthy procedure. Additionally, the ability to control and stabilize the catheter apparatus against the beating heart wall while creating channels with a laser is desirable for percutaneous procedures to ensure creation of channels as desired and to ensure that the laser is fired only within the myocardial tissue. TMR channels should be spaced and grouped appropriately to achieve the desired result without weakening or rupturing the heart muscle.

The early myocardial acupuncture procedures were not performed percutaneously. The Hardy $CO_2$ laser delivery system described above is rigid, relatively large, and not adaptable for percutaneous use. The Aita '316 patent does not suggest a method for percutaneous use of the laser delivery device described therein for surgical use.

U.S. Pat. No. 5, 389,096 issued Feb. 14, 1995 to Aita et al. purports to teach one method of percutaneous TMR using an elongated flexible lasing apparatus with control lines and a focusing lens structure at the distal tip. However, the method uses pressure applied manually to attempt to stabilize the apparatus against the wall of the heart, and no central, hollow passageway is described. No handle structure, modular or otherwise, is described nor are deflection, deflection components or a floating center tube.

Several prior art patents describe the use of catheters within the ventricle for percutaneous treatment of ventricular tachycardia. Such devices have a means to locate an arrhythmia site and ablate the site, at or just below the ventricle surface, using an electrode device or laser energy. U.S. Pat. No. 5,104,393 issued Apr. 14, 1992 to Isner teaches a catheter apparatus having a guiding Y-shaped sheath and guide catheter assembly for introducing an optical fiber into the ventricle. Positioning is described to enable a single burst of laser energy from a single aperture to ablate the site. However, positioning or specific steering means sufficient to create one or more TMR channels is not described or suggested.

U.S. Pat. No. 5,255,679 issued Oct. 26, 1993 and U.S. Pat. No. 5,465,717 issued Nov. 14, 1995 to, respectively, Imran and Imran et al., disclose non-laser, basket-shaped catheter apparatus for mapping and/or ablation of arrhythmia sites within the ventricle. A pull cable is used to expand the basket portion within the ventricle, and a plurality of electrodes on the arms of the basket are used for ablation. The basket device is designed to place the electrodes on the ventricle wall. Although the device allows for a fairly extensive mapping procedure without repositioning, no positioning means is provided for a laser delivery system to allow creation of TMR channels.

U.S. Pat. No. 5,114,402 issued May 19, 1992 to McCoy teaches a maneuverable distal apparatus with a temperature activated material of construction which, upon heating to a predetermined position, will assume a predetermined, memorized shape, and which upon cooling, will assume a different shape by action of a spring element urging the apparatus into the different shape.

U.S. Pat. No. 5,190,050 issued Mar. 2, 1993 to Nitzsche teaches a steerable catheter with a handle and a tube, the distal tip of which may be selectively curved by controllably moving one of three flat, sandwiched shims relative to the others by manipulation of a handle portion. However, deflection control requires the use of multiple shims, and no mechanism for integrated or otherwise fiber advance means is taught.

U.S. Pat. No. 5,358,479 issued Oct. 25, 1994 to Wilson, hereby incorporated herein in its entirety by reference, teaches another steerable catheter with a handle and a center tube, the apparatus having a single elongated, substantially flat shim spring mounted within the tip of the catheter tube, the shim having at least one transverse or lateral twist which causes the tip of the catheter tube to assume a desired curvature. However, Wilson does not teach the use of a hollow catheter for delivery of laser energy or any other functional device, nor does it contemplate the use of a floating center tube.

The use of superelastic and/or shape memory materials is widely known. *Structure and Properties of Ti—NI Alloys: Nitinol Devices & Components,* Duerig et al., In Press, Titanium Handbook, ASM (1994) In general, binary compositions of Nickel (Ni) and Titanium (Ti), yield alloys with shape memory and superelastic properties. These alloys are commonly referred to as Ni—Ti, nitinol, and other industry names. Their precise physical and other properties of interest are extremely sensitive to the precise Ni/Ti ratio used.

Generally, alloys with 49.0 to 50.7 atomic % of Ti are commercially available, with superelastic alloys in the range of 49.0 to 49.4%, and shape memory alloys in the range of 49.7 to 50.7%. Due to a rapid decrease in the ductility of the material, binary alloys with less than 49.4 at. % Ti are generally unstable. In general, these types of materials exhibit hysteresis, defined as a phenomenon exhibited by a system whose state depends on its previous history, and illustrated diagrammatically by the familiar upper and lower curves which meet at the ends and define an area under the curves. In the case of solid materials undergoing elastic hysteresis (as opposed to magnetic or electrical hysteresis), the curves are related to stress necessary to cause deformation or otherwise overcome existing stress in prestressed materials.

Properties of these materials change significantly as their respective "phase transformation temperatures" are approached. In general, at lower temperatures, these alloys will exist in a martensite state characterized as hard and easily deformed. However, in austenite, the high temperature phase, the alloys have a much higher yield and flow stresses. The addition of small amounts of third elements in the alloy can also have very significant effects on performance of the materials. Elements including but not limited to oxygen (O), nitrogen (N), iron (Fe), aluminum (Al), chromium (Cr), cobalt (Co) vanadium (V), zirconium (Zr) and copper (Cu), though having various effects on the Ni—Ti matrix, can have the tendency to increase strength, increase stiffness, control hysteresis and/or decrease or increase phase transition temperatures.

Ni—Ti products are commonly used in the form of cold drawn wire or as barstock. Tubing is also available. The toxicity of the alloy or the solubility or other compatibility with the biological environment in which catheter equipment is used is an important consideration. The alloys are commonly used in a cold worked and partially annealed condition. The partial anneal does not recrystallize the material but does bring about the onset of recovery processes. The extent of the post-cold worked recovery depends upon many aspects of the application, such as the desired stiffness, fatigue life, ductility, recovery stress, etc. Ni—Ti is difficult to join since most mating materials cannot tolerate the large strains experienced by Ni—Ti. Most connections will rely on crimped bonds. Although Ni—Ti can be brazed or welded to itself with relative ease, such as by resistance and with TIG methods, brazing or welding to other materials is difficult though proprietary methods do exist and are practiced in large volumes, for example in the production of eyeglass frames.

For the purposes of this disclosure, a distinction between superelastic materials and shape memory materials is made. Stuperelasticity refers to the highly exaggerated elasticity, or springback, observed in many Ni—Ti alloys deformed at a specific temperature. The function of the material in many of such cases is to store mechanical energy. Though limited to a rather small temperature range, these alloys can deliver over 15 times the elastic motion of a spring steel, i.e., withstand a force up to 15 times greater without permanent deformation. Shape memory materials will refer to those materials which can be deformed, but which will freely recover their original shapes during heating, often utilizing electrical resistivity, or which will develop a large recovery stress when recovery is prevented. With regard to the present invention, it will be understood that the transition temperature of materials must, in general, be somewhat above body temperature.

U.S. Pat. No. 3,890,977 issued Jun. 24, 1975 to Wilson teaches kinetic memory electrodes, catheters and cannulae.

These devices incorporate a material, such as a Ni—Ti alloy, having heat-activated mechanical memory properties. The device is formed into an operative shape at a high temperature. Then, at a low temperature below its transitional temperature, it is reformed into a shape for ease of insertion into a guide catheter or the like or otherwise through a portion of a patient's vasculature or other body lumen. When located in the organ or other desired region, those portions of the device constructed using such shape memory materials are heated to above their transitional temperatures, using electrically resistive elements, thereby returning the catheter to its original annealed anchoring or proper locating shape. An important drawback of the Wilson apparatus is that heat must be applied to the catheter tip. Complicated construction and electrical power distribution must be considered.

As can be seen from a description of the prior art above, percutaneous TMR steerable catheters are virtually unknown with the exception of the catheter briefly described in the '096 Aita patent. There is a need in the art for a percutaneous TMR steerable catheter which has means for easily steering, positioning and repositioning the steerable catheter on the ventricle wall, and having a port for a laser delivery means to enable rapid creation of one or more appropriately grouped and spaced TMR channels.

ADVANTAGES AND SUMMARY OF THE INVENTION

Thus, it is an advantage of the present invention to provide a steerable catheter and method of use for percutaneous and other intra-vascular procedures, including TMR, or any stimulation procedure, which overcomes the limitations of the prior art.

It is a further advantage of the present invention to provide a steerable catheter capable of being guided into a heart chamber and used therein for creating a plurality of TMR channels controllably and efficiently.

It is a further advantage of the present invention to provide an elongated steerable catheter for placement within a heart chamber, organ aperture or other body opening, the steerable catheter having at least one center tube with hollow passageway extending therethrough, the center tube for guiding a laser delivery means or other functional device to selected surfaces of the heart chamber, organ aperture or other body opening for laser or other treatment thereon, particularly adapted for laser-assisted transmyocardial revascularization (TMR).

It is yet a further advantage of the present invention to provide a percutaneous steerable catheter which can be positioned securely into a selected position within the left ventricle, or other body opening or cavity.

A further advantage of the present invention is to provide a steerable catheter to enable creation of a plurality of appropriately grouped and spaced TMR channels on a selected surface within a body cavity or organ quickly and safely.

Yet an additional advantage of the present invention is to provide a modular steerable catheter system capable of being assembled and operated as desired, comprising one or more modular assemblies which can be coupled together for operation in unison, including but not limited to a central, modular steerable catheter with a deflectable end portion, a modular fiber advance handpiece unit, and other functional devices including fiber advance depth control mechanism, visualization means, etc.

Therefore, to summarize, an elongated steerable catheter for placement within a heart chamber, organ aperture or other body opening and having at least one center tube with hollow passageway for guiding a laser delivery means or other functional device to selected surfaces of a heart chamber, organ aperture or other body cavity for laser or other treatment thereon, particularly adapted for laser-assisted percutaneous transmyocardial revascularization (TMR), is disclosed herein. The steerable catheter has a handle portion at its proximal end and a controllably deflectable portion at its distal end.

The elongated center tube has a distal end, in the region where a curvature is to be formed, and a shim anchor sleeve is slidably disposed over the center tube. The shim anchor sleeve is attached to the inside wall of the outer jacket. A bendable shim member extends between the distal tip of the steerable catheter and the sleeve surrounding the center tube. Opposite the shim is a guide for a pull cable, the pull cable attached to the distal end of the steerable catheter and extending through the guide to the handle. Thus, the shim is maintained radially opposite the pull cable with the center tube in between.

An outer jacket has, in a preferred embodiment, distinct sections of different stiffness or durometer. One or more distinct sections of material of differing stiffness or durometer can be used. Junctions between the sections of different stiffness or durometer can be discrete and clearly defined, or they can blend smoothly or get more or less flexible gradually. A distal, more flexible portion is coupled to a proximal, stiffer portion. The shim anchor sleeve is coupled to the outer jacket at or near the junction of two portions of the outer jacket. Thus, the center tube moves freely through the shim anchor sleeve.

Adjacent the handle, the proximal outer jacket portion terminates at the catheter base. The pull cable extends through the catheter base, through a deflection housing tube, and terminates in a cable stop. Rotation of a deflection knob threadably mounted onto the deflection housing tube will cause the pull cable to be pulled backward, or the outer jacket to be pushed forward, relative to each other, thereby inducing deflection of the distal end of the steerable catheter.

The elongated steerable catheter is designed to be placed into the vasculature of the patient and steered therethrough until the distal tip is adjacent a selected portion of tissue, such as on an endocardial surface within the left ventricle. Thus, the distal tip of a laser delivery means, such as an optical fiber or fiber bundle or other functional device, can be extended through the center tube of the steerable catheter such that its distal tip comes into contact with the selected surface structure for treatment thereon. With regard to TMR therefore, the laser delivery means can be controllably advanced through the steerable catheter for creating one or more TMR channels. Furthermore, with regard to non-laser TMR, a cannula or trocar assembly may be extended through the steerable catheter into the tissue of the left ventricle, with or without use of a mechanical piercing tool.

In a preferred embodiment, the invention is a modular steerable catheter system capable of being assembled and operated as desired, comprising one or more modular assemblies which can be coupled together for operation in unison, including but not limited to a central, modular steerable catheter with a deflectable end portion, a modular fiber advance handpiece unit, and other functional devices including fiber advance depth control mechanism, visualization means, drug delivery apparatus, etc.

Numerous other advantages and features of the present invention will become readily apparent from the following detailed description of the invention and the embodiments thereof, from the claims and from the accompanying drawings.

BRIEF DESCRIPTION OF THE DRAWINGS

FIG. 13B is a representative section view of the deflection means of a preferred embodiment of the steerable catheter of the present invention shown removably coupled to the distal end of a fiber advance component.

FIG. 14A is a representative section view of a proximal end of the steerable catheter of the present invention.

FIG. 15 is a representative isometric view of a drug delivery apparatus coupled to the proximal end of the modular handle of a steerable catheter of the present invention.

DETAILED DESCRIPTION OF THE PREFERRED EMBODIMENT

Preferred Apparatus

Figure 1:
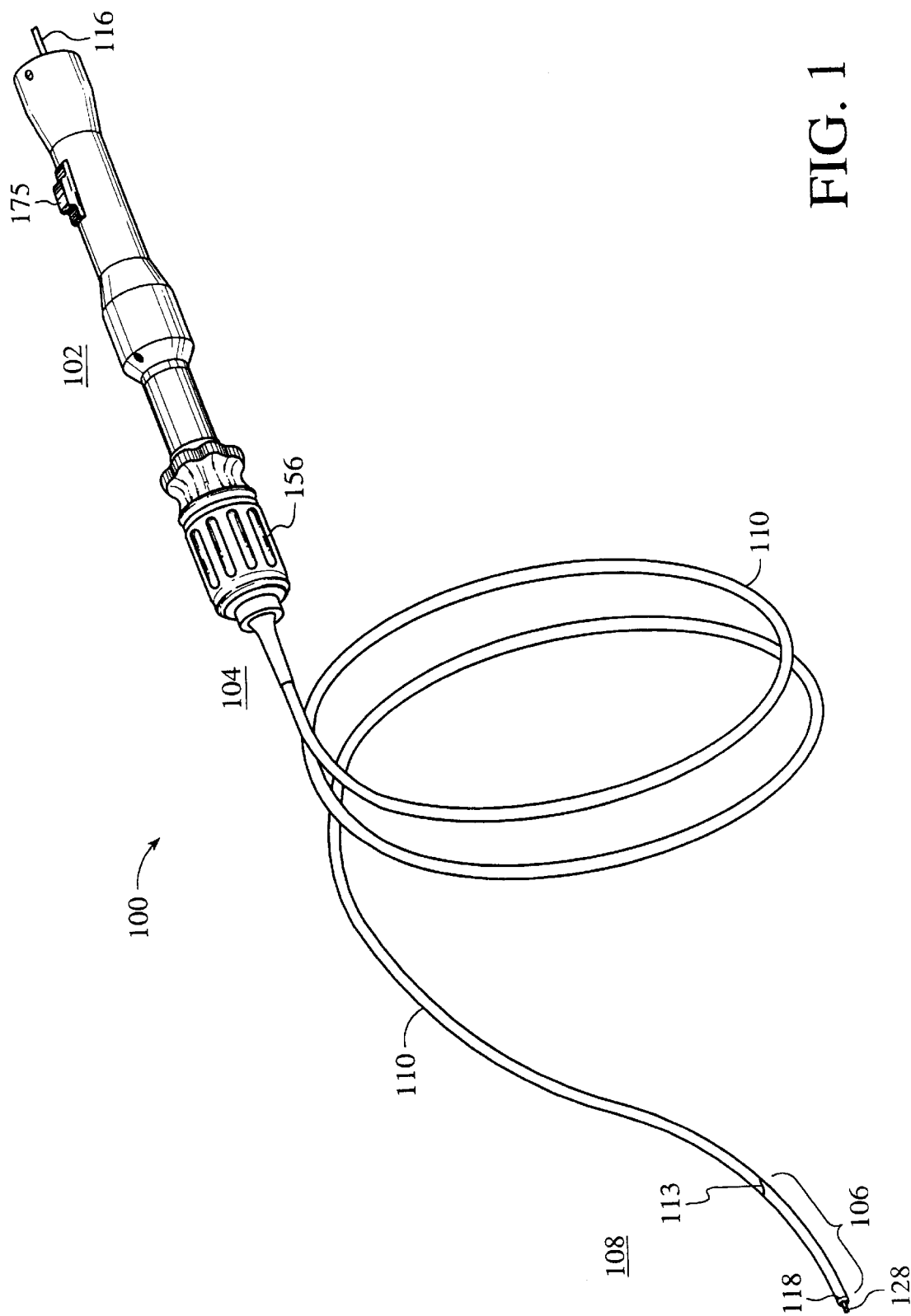
FIG. 1 is a representative isometric view of the steerable catheter of the present invention showing a modular handle having a deflection component and fiber advance component.

FIG. 1 is a representative isometric view of the steerable catheter 100 of the present invention showing a modular handle having a deflection component and a fiber advance component. A preferred embodiment of the steerable catheter 100 has a modular handle 102 at its proximal end 104 and a controllably deflectable end portion 106 at its distal end 108. The elongated central torquing portion 110 is somewhat flexible and enables torquing and steering. The deflectable end portion 106 is more flexible than the elongated central torquing portion 110, allowing the deflectable end portion 106 to develop a controlled bend with a smaller radius of curvature.

Figure 2:
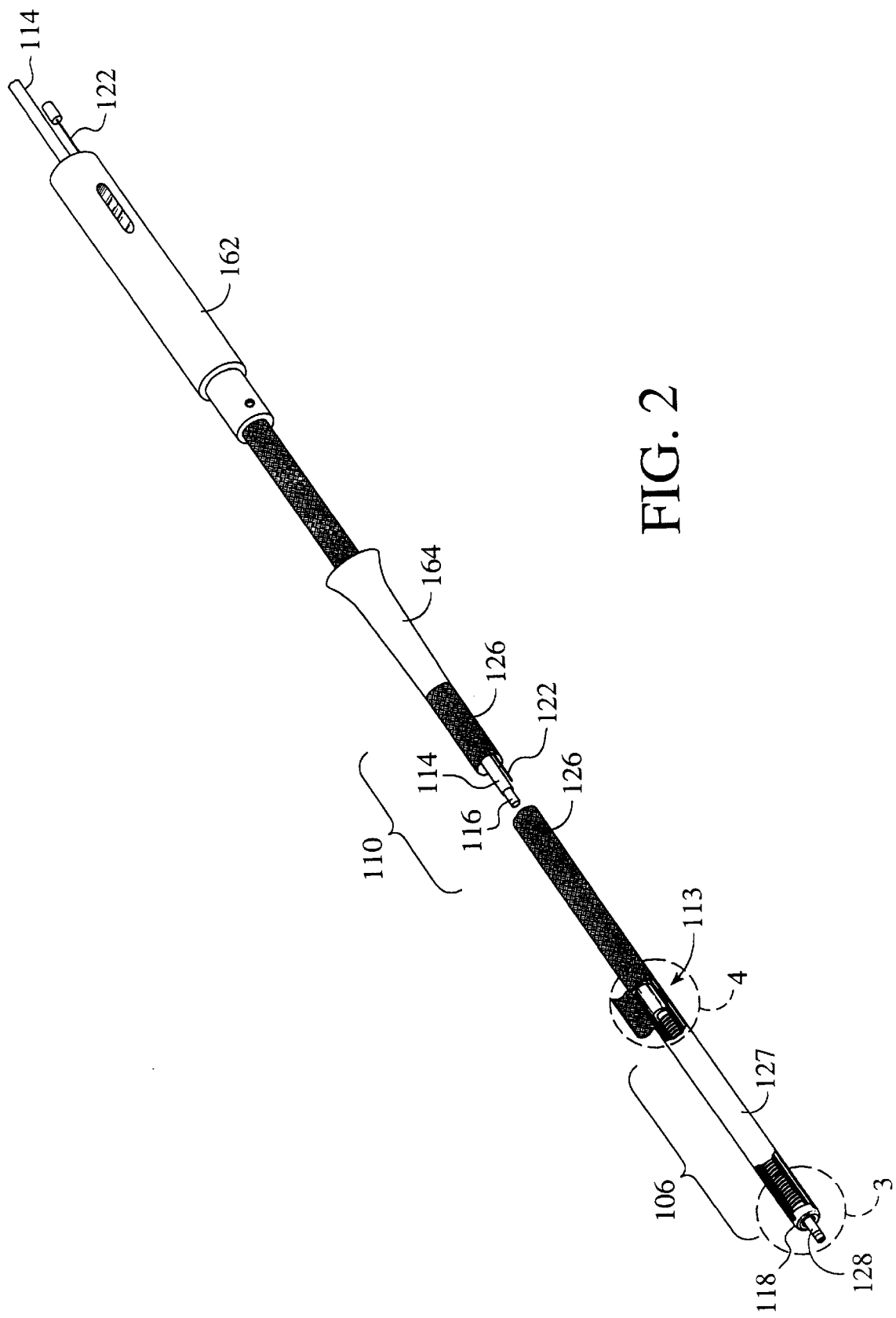
FIG. 2 is a representative isometric view of the deflectable end portion of the steerable catheter with the shim anchor sleeve in a breakaway view of a preferred embodiment of the steerable catheter of the present invention and shown without the deflection knob.
Figure 3:
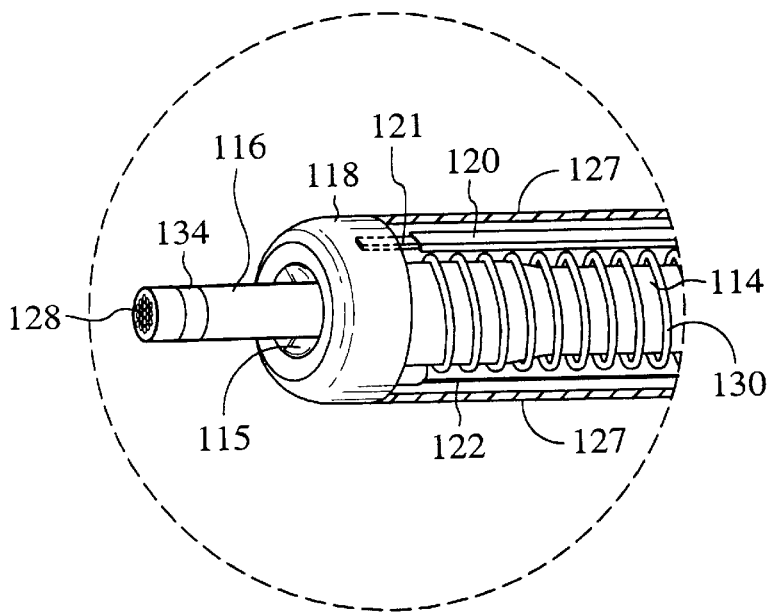
FIG. 3 is a representative cutaway isometric view of detail 3 showing the distal tip of a preferred embodiment of the steerable catheter of the present invention.
Figure 4:
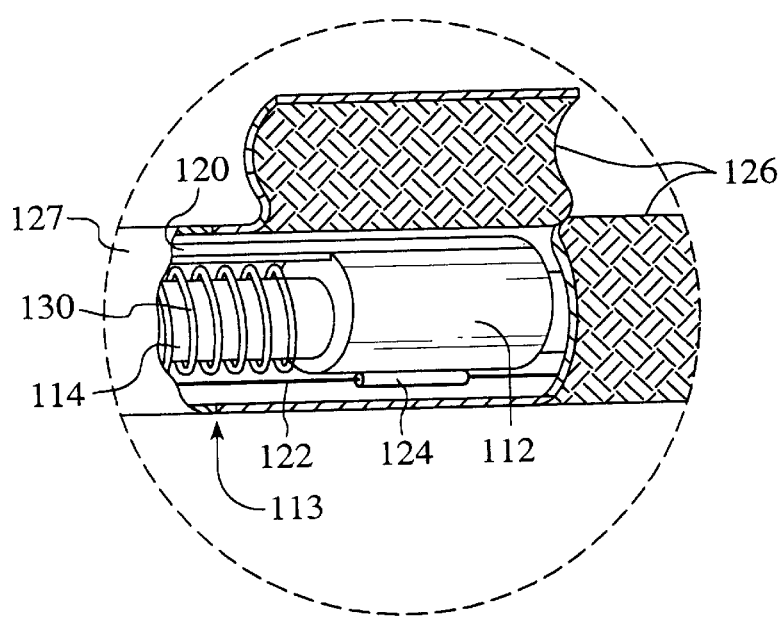
FIG. 4 is a representative isometric view of detail 4 showing shim anchor sleeve keyed to inside of the outer jacket and located adjacent the junction between different types of outer jacket construction of the steerable catheter of the present invention.

FIG. 2 is a representative isometric view of the deflectable end portion 106 of the steerable catheter 100 in breakaway view and shown without the deflection knob 180. FIG. 3 is a cutaway view of detail 3 showing the distal tip 118 of a preferred embodiment of the steerable catheter 100 and FIG. 4 is a view of detail 4 showing a shim anchor sleeve 112 keyed to inside and prior to attachment to of the outer jacket and located adjacent the junction 113 between the deflectable end portion 106 and the elongated central torquing portion 110 of the steerable catheter 100 of the present invention. The proximal outer jacket portion 126 extends from the distal end of the modular handle 102 to the junction 113 and distal outer jacket portion 127 extends from the junction 113 to distal tip 118 of the steerable catheter 100.

A center tube 114 extends at least partially through the steerable catheter, and is attached at one end to the distal tip 118 of the steerable catheter. The proximal end of the center tube 114 is free and floats within the modular handle, thereby allowing the center tube 114 to slide and move during deflection of the distal tip 118 of the steerable catheter 100. The center tube 114 defines a hollow, central passageway 115 through the center tube 114 for insertion of a tool such as an optical fiber for transmission of laser energy, or other functional device. The tubular material of construction of the center tube 114, such as, but not limited to, Polypropylene or other polymeric material will resist collapse during bending and twisting, and will resist collapse by external forces. At the distal end of the center tube 114 the distal tip 118 is contoured and/or polished to minimize any adverse effect, such as trauma caused by motion of the tip through a body lumen, cavity or opening, or by loss of maneuverability and control thereof.

As best shown in FIGS. 3 and 4, the center tube 114 slidably extends through the shim anchor sleeve 112 which is attached to the inner wall of the outer jacket. The shim anchor sleeve 112 is coupled to the distal portion of the steerable catheter with, and provides support for, a flat, semi-rigid shim 120 which extends between the distal tip 118 and the shim anchor sleeve 112. The flat shim 120 defines a plane out of which the shim 120 can be deflected upon the application of lateral force, but back into which the shim 120 will return with spring-like action on release of the deforming force. A tang 121 at the distal end of the shim 120 serves to anchor the shim 120, such as by soldering, to the distal tip 118. As will be described later in greater detail, the purpose of the shim anchor sleeve 112 is to allow free movement of the center tube 114 within the outer jackets 126 and 127, to support and position the center tube 114, as well as to serve as an anchor point for shim 120 and a guide for a pull cable 122.

Proximal outer jacket portion 126 covers the center tube 114 adjacent the elongated central torquing portion 110 and distal outer jacket portion 127 covers the assembly adjacent the deflectable end portion 106. Further, it will be understood that laser delivery means 116, or other functional device, can be slidably disposed inside center tube 114 such that a distal tip 128 of laser delivery means 116 can be advanced through the distal tip 118 of center tube 114 to surfaces or structures for laser treatment thereon. Optionally, the proximal outer jacket portion 126 can be made of a braided or "laid-up" type of construction. The braided construction will enhance resistance to sidewall collapse, facilitate torquing and twisting, and provide enhanced columnar support during deflection. The shim anchor sleeve 112 is proximal the joint 113, and in a preferred embodiment the entire shim anchor sleeve 112 is bonded to the inside wall within the proximal outer jacket portion 126 adjacent the junction 113 with the distal outer jacket portion 127. It will be understood that the precise length and point of connection between the shim anchor sleeve 112 and the outer jackets is selectable as desired, but that the design must not interfere with or otherwise impair normal operation of the junction 113.

Pull cable 122 extends from the distal tip 118, where it is fixedly attached, through pull cable guide 124 or other retaining aperture in shim anchor sleeve 112. By positioning pull cable guide 124 axially opposite shim 120, the pull cable 122 is caused to deflect distal tip 118, thereby bending shim 120. The pull cable 122 passes through pull cable guide 124 and extends to modular handle 102 where it can be controllably pulled and released by a deflection component, as desired, to cause selective deformation of the deflectable end portion 106 of the steerable catheter 100 of the present invention.

Figure 6:
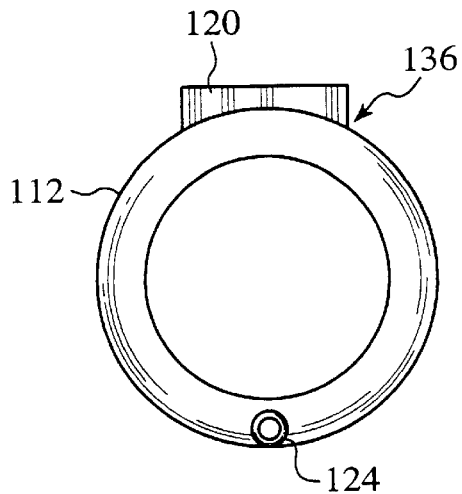
FIG. 6 is a representative end view of a preferred embodiment of the shim anchor sleeve of the steerable catheter of the present invention.

FIG. 6 is a representative end view of a preferred embodiment of the shim anchor sleeve 112 of the steerable catheter 100 of the present invention. The shim 120 is linked to shim anchor sleeve 112 at shim attachment point 136, radially opposite or otherwise operatively spaced relative to pull cable guide 124.

As best shown in FIGS. 3 and 4, a helical coil spring 130 preferably is wrapped around at least portions of the center tube 114. Helical coil spring 130 has several functions, one of which is to provide enhanced visualization. By constructing helical coil spring 130 of platinum or other radiopaque material, the precise angle of deflection as well as geometric positioning of the deflectable end portion 106 can be determined using fluoroscopy. Another function of helical coil spring 130 is to impart additional sidewall strength to the tubing material of center tube 114, especially important in the deflectable end portion 106 portion of the steerable catheter 100 during temporary steering, twisting, and bending deformations to prevent sidewall collapse. Proper selection of the stiffness and number and placement of individual coils will determine the bend radius of the deflectable end portion 106 and its distance from the distal tip 118 of the center tube 114. Furthermore, by using superelastic or shape memory materials of construction, as will be further discussed below, the deflectable end portion 106 can be given some predetermined curvature.

In an additional preferred embodiment, the center tube 114, shim 120, proximal and distal outer jacket portions 126 and 127 and/or the helical coil spring 130 are preferably made at least partially of, or otherwise comprise, a superelastic material which can be given a selected shape. Other suitable materials include platinum, spring steel, stainless steel, shape memory or superelastic/shape memory alloys. Once a superelastic material has been shaped, it has a memory for the shape. Upon deformation from the preformed shape, the material will tend to independently return to its preformed shape with spring-like action. Thus, the deflectable end portion 106 of the steerable catheter 100 can be temporarily deformed or otherwise curved so as to steer and position the deflectable end portion 106 of the steerable catheter 100 through the vasculature and inside the left ventricle or other body opening, and against the heart wall.

In the case of shape memory materials, a "memory" for a preformed shape can be temperature set in the deflectable end portion 106 of the steerable catheter 100. The percutaneous steerable catheter can be straightened temporarily and extended through the vasculature. Once the steerable catheter is in position, memory recall of the original preformed shape can be produced by any of a number of different ways. These include heating using electrically resistive material, electrically sensitive material, radio frequencies, circulating heated fluid, etc. It will also be understood that the center tube 114 of the steerable catheter 100 can also act as a type of "hypo" tube, and an additional tube inside the center tube or annularly inside or outside the center tube for delivery of fluids, other tools, etc. can be used. Furthermore, by providing distinctive cross section geometries, components can be "keyed" together as desired, to prevent undesired rotation of one or the other component, as well as to provide rotational control to the physician.

Figure 5:
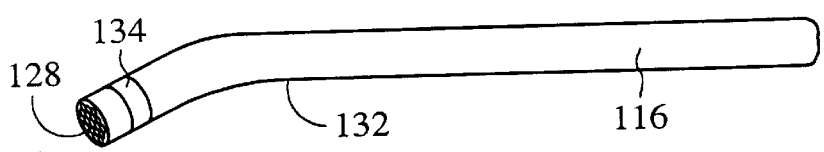
FIG. 5 is a representative isometric view of the distal end of a laser delivery means of the present invention.

FIG. 5 is a representative isometric view of the distal tip 128 and distal end 132 of a laser delivery means 116 of the present invention. The distal end 132 of the laser delivery means 116 optionally may be provided with a slight deflection or curvature. It will be understood that the slight curvature of the distal end 132 of laser delivery means 116 can be made in any of several different ways, including a permanent curvature formed by heat, molding, laminated construction, etc., or a temporary curvature formed otherwise.

Radiopaque marker 134 adjacent the distal tip 128 of laser delivery means 116 is particularly useful in visualization via fluoroscopy or other methods. Such marker 134 can be made of platinum or other suitable radio-opaque material. Thus, the precise location of the distal tip 128 of laser delivery means 116 can be determined. It will be understood that visualization enhancement aids, including but not limited to radiopaque markers, tantalum and/or platinum bands, foils, strips may be placed on the various components of the present invention, including on the deflectable end portion 106, helical coil spring 130, and other parts of the steerable catheter 100, or at any position on laser delivery means 116, such as optical fiber or fiber bundle, or other functional device, will be very helpful in visualization of the percutaneous procedure.

It will be understood hereby, with particular regard to FIGS. 7–9B as well as throughout this treatment, that various embodiments of various aspects of the present invention will be referred to by common reference numerals, for convenience and to indicate similar general purpose, despite the described structural variations and others included within the scope of the present invention.

Figure 7:
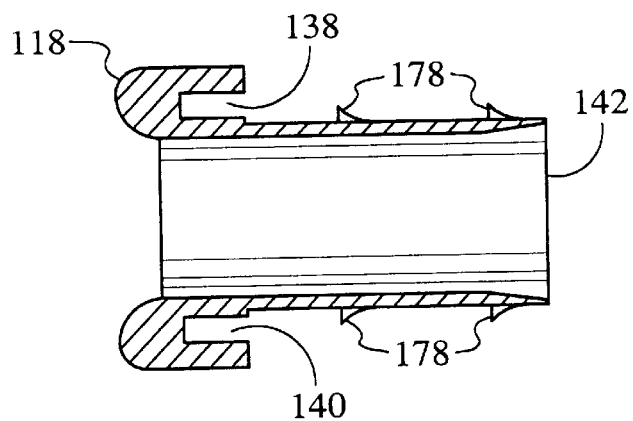
FIG. 7 is a representative section view of a preferred embodiment of the distal tip of the steerable catheter of the present invention.

FIG. 7 is a representative section view of a preferred embodiment of the distal tip 118 of the steerable catheter 100 of the present invention. First attachment point 138 and second attachment point 140 are operatively positioned radially opposite each other on the distal tip 118, serving to couple the shim 120 and pull cable 122 to shim anchor sleeve 112. Proximal end 142 attaches to center tube 114 and forms the distal end of deflectable end portion 106. As shown, spaced radial barbs 178 serve to anchor the distal tip 118 into the center tube 114.

Figure 8A:
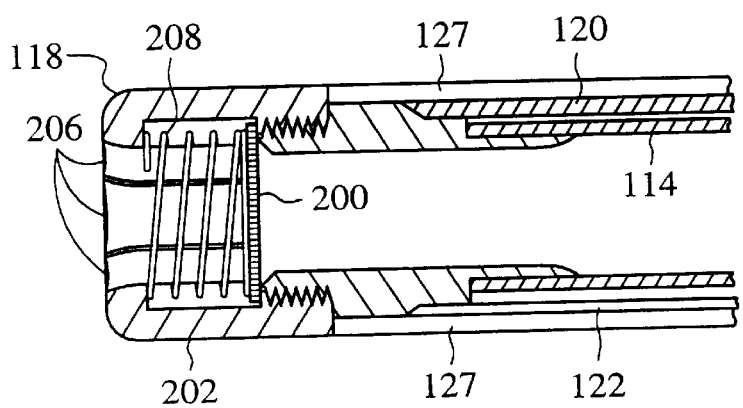
FIG. 8A is a representative section view of a preferred embodiment of a piercing means in a retracted position in the distal tip of the steerable catheter of the present invention.
Figure 8B:
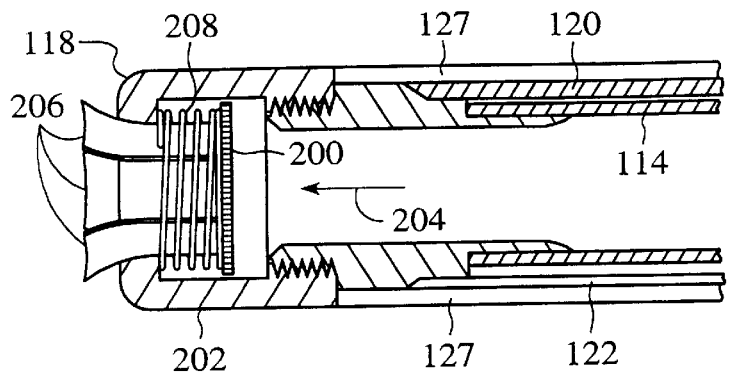
FIG. 8B is a representative section view of a preferred embodiment of a piercing means in a protracted position in the distal tip of the steerable catheter of the present invention.
Figure 8C:
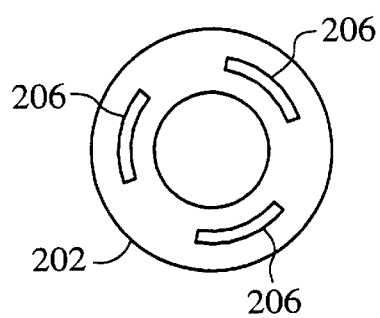
FIG. 8C is a representative end view of a preferred embodiment of a piercing means in the distal tip of the steerable catheter of the present invention.

FIG. 8A is a representative section view of a preferred embodiment of a piercing means in a retracted position in the distal tip 118 of the steerable catheter 100 of the present invention. FIG. 8B is a representative section view of a preferred embodiment of a piercing means in an extended position in the distal tip 118 of the steerable catheter 100 of the present invention. FIG. 8C is a representative end view of a preferred embodiment of a piercing means in the distal tip 118 of the steerable catheter 100 of the present invention. Pressure plate 200 is retained by threadable end cap 202 threaded onto or otherwise coupled to the distal tip 118 of the steerable catheter 100. When a force is applied to pressure plate 200 in direction 204, anchoring teeth 206 will be extended as shown in FIG. 8B. When the force is released, biasing spring 208 will reposition pressure plate 200 as shown in FIG. 8A and retract anchoring teeth 206.

As shown in FIG. 8C, the operative spacing and shape of anchoring teeth 206 can be selected as desired. The piercing tip is especially useful for mechanically piercing the endocardial surface of the left ventricle, when introduced thereinto percutaneously. Mechanically piercing the surface of openings, body cavities or other tissue structures will also serve to anchor the deflectable end portion 106 of the steerable catheter 100 in a given position for laser or other treatment thereon, effected via the steerable catheter 100, such as through the center tube 114.

Figure 9A:
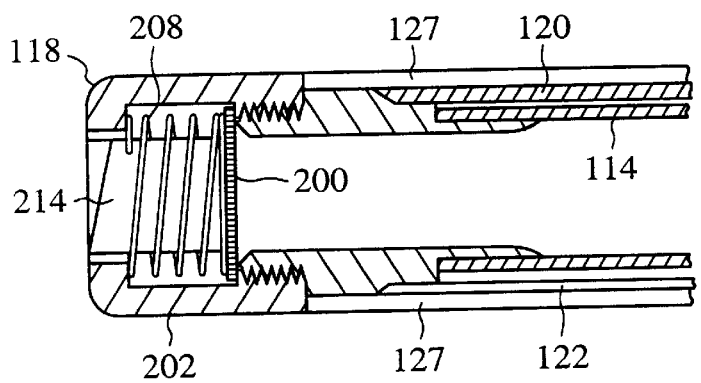
FIG. 9A is a representative section view of another preferred embodiment of a piercing means in a retracted position in the distal tip of the steerable catheter of the present invention.
Figure 9B:
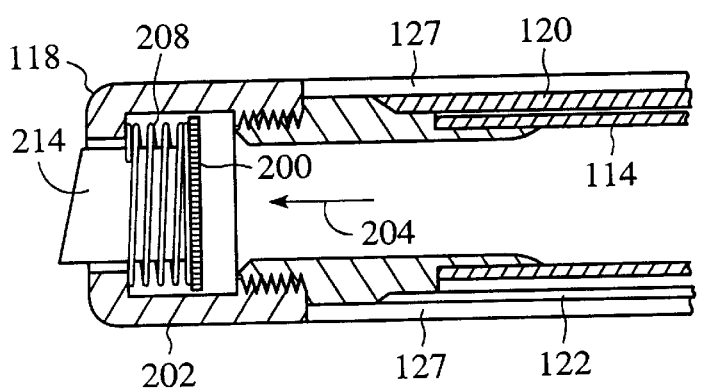
FIG. 9B is a representative section view of another preferred embodiment of a piercing means in a protracted position in the distal tip of the steerable catheter of the present invention.

FIG. 9A is a representative section view of another preferred embodiment of a piercing means in a retracted position in the distal tip 118 of the steerable catheter of the present invention. FIG. 9B is a representative section view of another preferred embodiment of a piercing means in an extended position in the distal tip 118 of the steerable catheter of the present invention. As in FIGS. 8A–8C, helical coil biasing spring 208 and pressure plate 200 are retained disposed adjacent distal tip 118 of the steerable catheter 100 by end cap 202. As pressure plate 200 is moved in direction 204, as by internal pressure or force created by fluid, rods or other biasing means, piercing tube 214 will be extended as shown in FIG. 9B. When the pressure or force is removed, biasing spring 208 will return piercing tube 214 to within the distal end of the piercing means assembly. Additional anchor/piercing means designs, including multiple individual solid or hollow needles, flat blades, curved blades, etc. will be included within the scope of the present invention. Therefore, it is understood that piercing tips may be activated by applying pressure to pressure plate, using flushing fluids as an example, through center tube 114, or the piercing means may be attached to a tube which extends to the handle for control at the proximal end. In such embodiment, the pressure plate may be omitted, and the spring is useful but optional.

Figure 11:
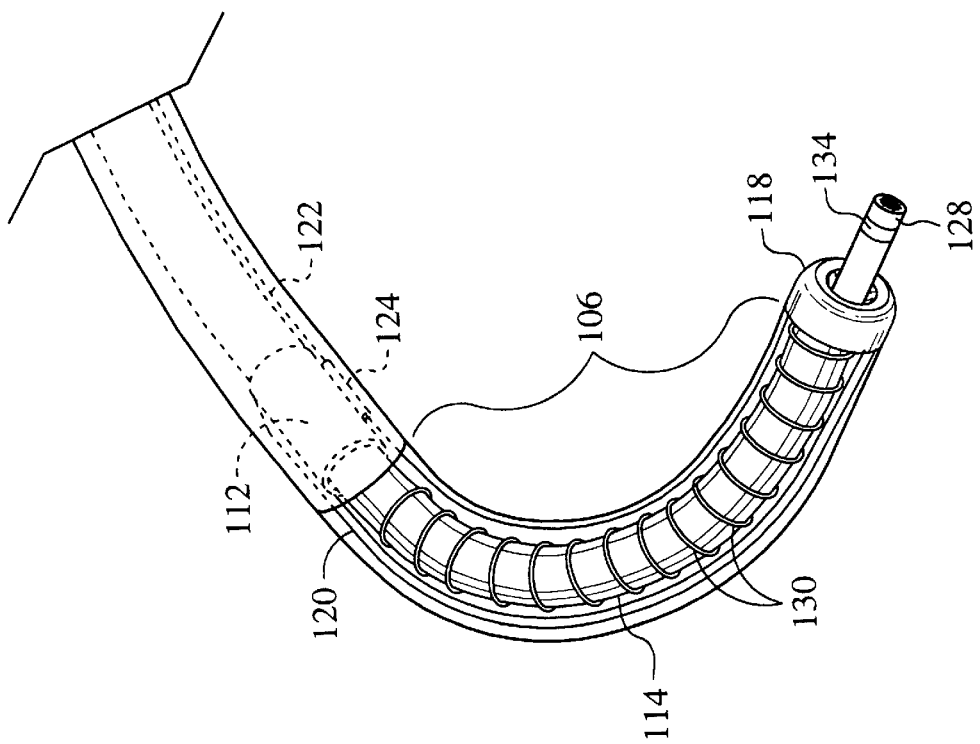
FIG. 11 is another representative isometric view of the distal end and shim anchor sleeve of another preferred embodiment of the steerable catheter of the present invention.
Figure 10:
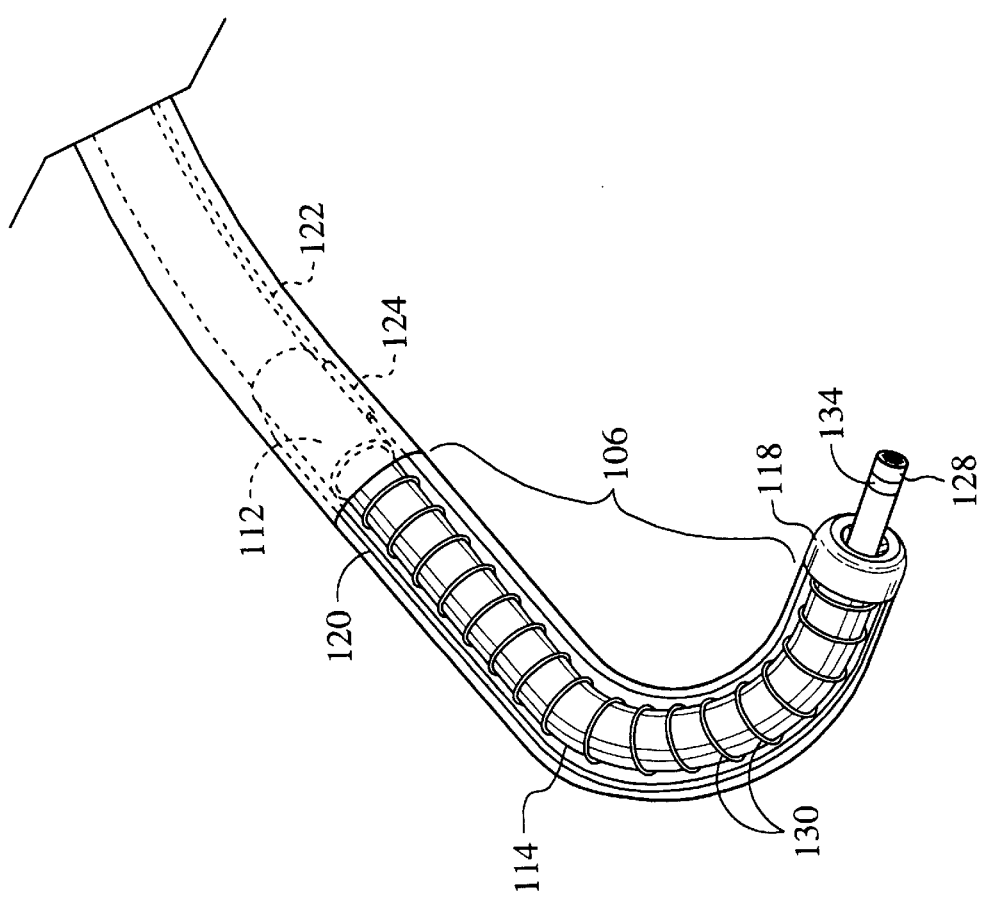
FIG. 10 is a representative isometric view of the distal end and shim anchor sleeve of a preferred embodiment of the steerable catheter of the present invention.

FIG. 10 is a representative isometric view of the deflectable end portion 106 and shim anchor sleeve 112 of a preferred embodiment of the steerable catheter 100 of the present invention. FIG. 11 is another representative isometric view of the deflectable end portion 106 and shim anchor sleeve 112 of another preferred embodiment of the steerable catheter 100 of the present invention. As will be understood by the drawings and description herein, the curvature in the deflectable end portion 106 of the center tube 114 can be positioned as desired at any point. The helical coil spring 130 can be constructed with varying degrees of flexibility, and with any number of coils, such that the curvature can be moved closer to the distal tip 118 of the center tube 114 or closer to the shim anchor sleeve 112, as desired as shown, respectively, in FIGS. 10 and 11. As will be understood, increasing the tension in pull cable 122 by retraction thereof will cause deflection of the distal tip 118 and the deflectable end portion 106 in a direction essentially out of, and into and toward a position perpendicular to, the plane of the shim 120. Continued retraction of the pull cable 122 will cause continued deflection of the distal tip 118 of the steerable catheter, with useful ranges of deflection between about 0 and about 180 degrees (U shape) to about 270 degrees (pig-tail shape), or more or less depending upon construction. Additionally, by allowing the center tube 114 to remain free at its proximal end, maximum deflection is possible without undo strain on the center tube 114 which can slide forward within the handle.

Additionally, as described above, by utilizing materials with varying durometer and by varying the number and density of coils and by varying the stiffness of the helical coil spring used, the center tube 114 can be designed to bend at a predetermined or selected point within the deflectable end portion 106. Such point can be immediately adjacent the distal tip 118, between the distal tip 118 and the shim anchor sleeve 112, and or adjacent the shim anchor sleeve 112 itself.

Figure 12:
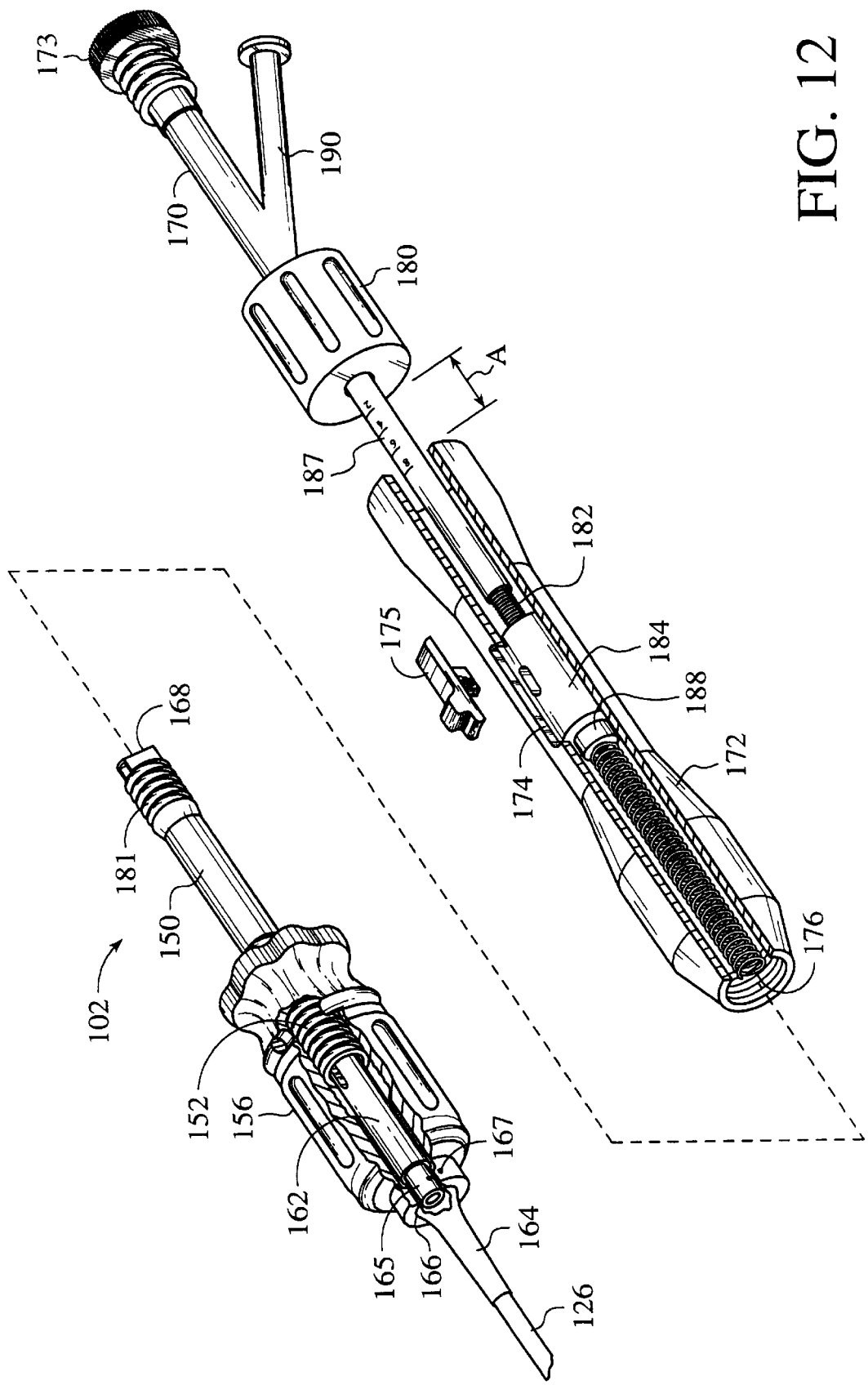
FIG. 12 is a representative partially cut-away and partially exploded view of the modular handle showing a fiber advance means component and a deflection component.
Figure 13A:
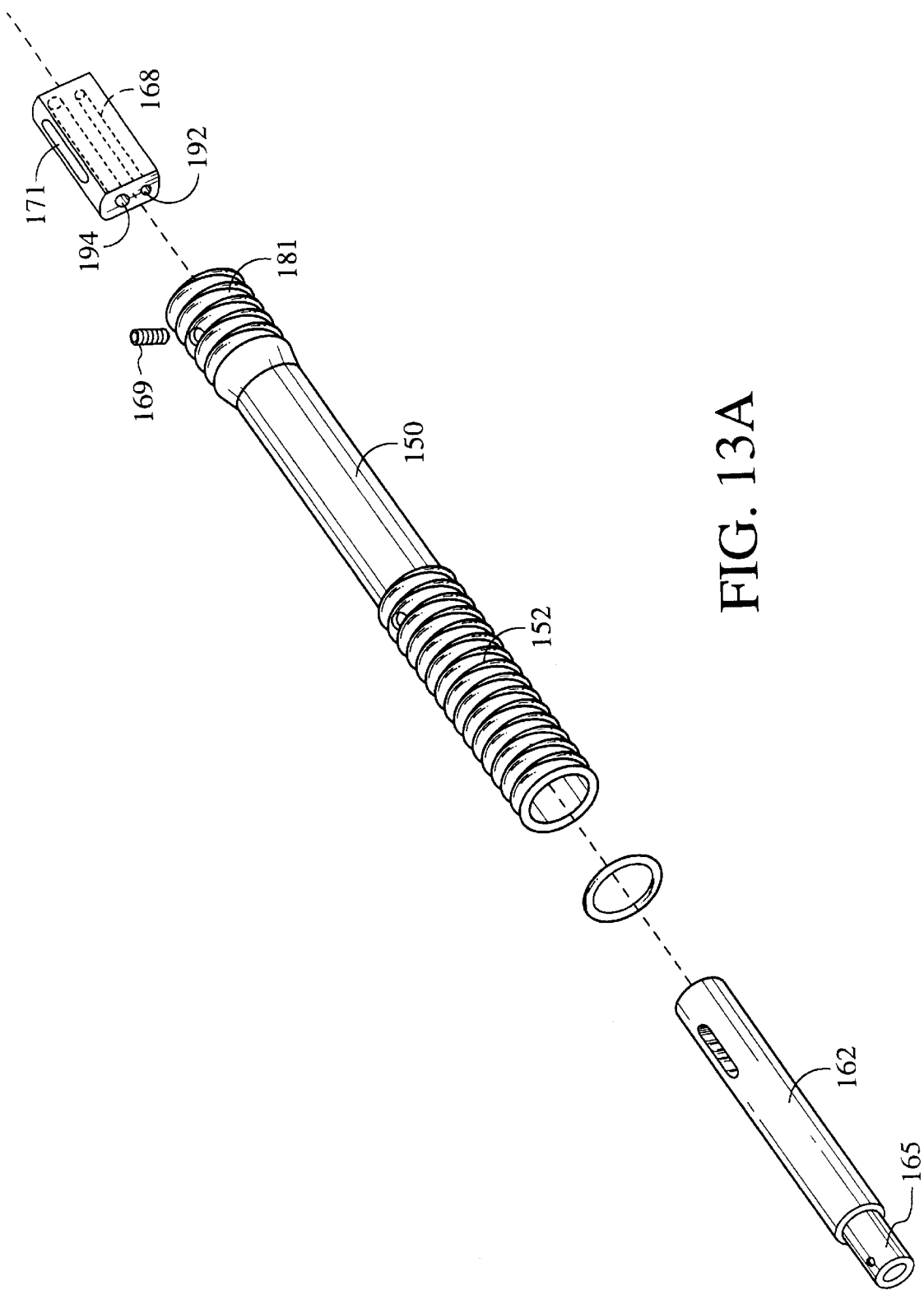
FIG. 13A is a representative exploded view of the internal assembly of a deflection means component of a preferred embodiment of the steerable catheter of the present invention.
Figure 14B:
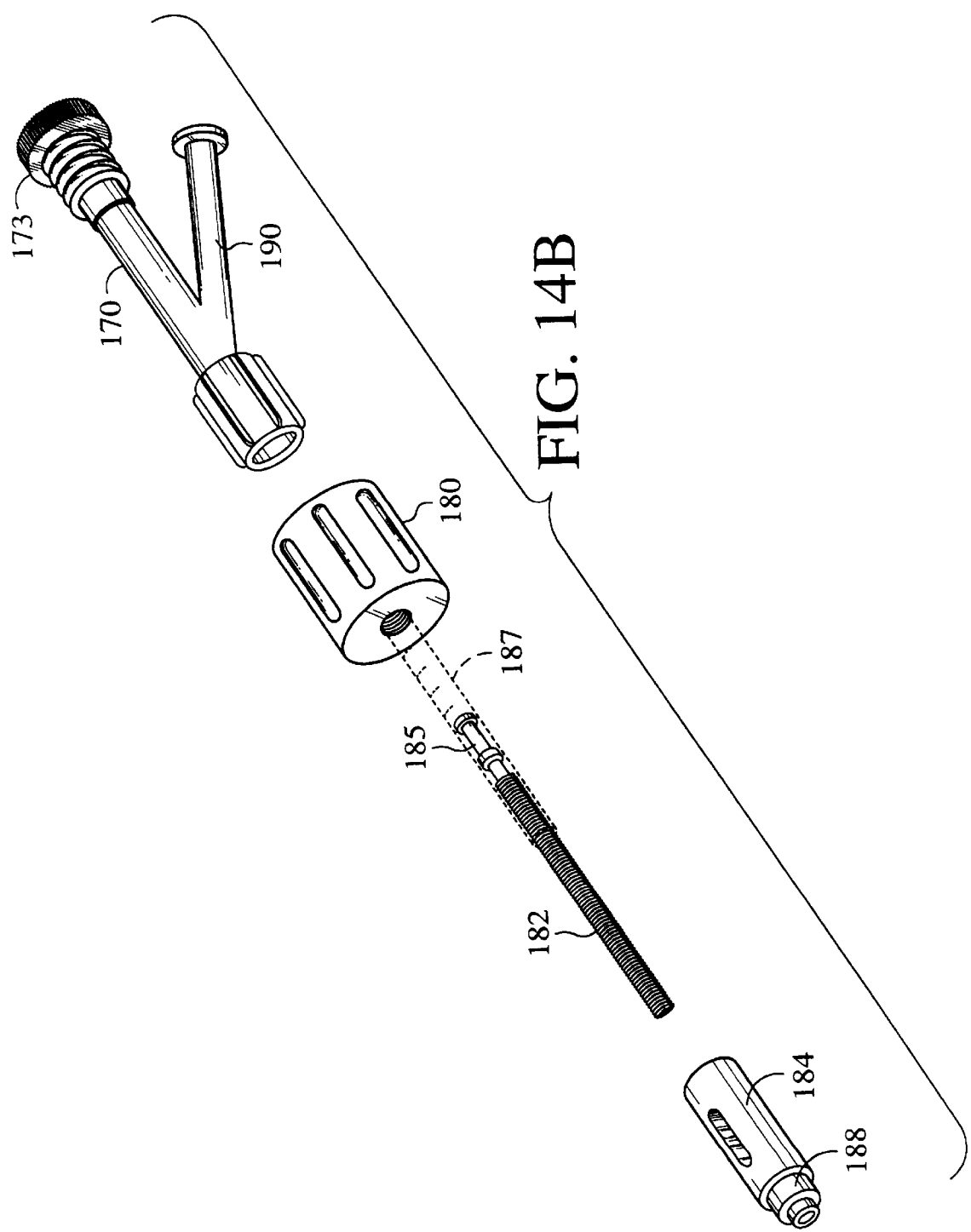
FIG. 14B is a representative exploded view of the depth stop means of the steerable catheter of the present invention.

FIG. 12 is a representative partially cut-away and partially exploded view of the modular handle 102 showing a fiber advance means component and a deflection component. FIG. 13A is a representative exploded view of the internal assembly of the deflection component and FIG. 13B is a representative section view of the deflection component coupled to a fiber advance handle of the steerable catheter 100 of the present invention shown removably coupled to the distal end of a fiber advance mechanism. FIG. 14A is a representative section view of a proximal end of the steerable catheter 100 of the present invention. FIG. 14B is a representative exploded view of the depth stop means of the fiber advance mechanism of the steerable catheter 100 of the present invention. It will be understood that structural elements with like reference numerals, as described herein with reference to the drawings, are identical or similar to each other.

Referring now to FIGS. 12–13B, proximal outer jacket portion 126 terminates at its proximal end and is coupled to a distal, inside stepped portion 165 of catheter base 162 by setscrew 167, or by other means including adhesive, etc. An optional strain relief 164 is fastened to either or both the proximal catheter jacket 126 or to the distal, stepped portion 165 and/or the catheter base 162, or is otherwise coupled thereabouts, such as by setscrew 167, and serves to minimize the effect of deflection or other handling of the elongated central torquing portion 110 and deflectable end portion 106 on the modular handle 102 and deflection mechanism. A retaining collar 166 is provided around the strain relief 164 and distal, stepped portion 165. A hollow, tubular deflection housing tube 150 houses the catheter base 162 and has a first one or more external helical threaded portion 152 located at the distal end of the deflection housing tube 150. Deflection knob 156 with corresponding helical threads located on an inner, annular surface is threadably coupled to threaded portion 152 at the distal end of deflection member 150. Thus, deflection knob 156 is able to rotate on threaded portion 152 above catheter base 162, retained in place by retaining collar 166, thus maintaining the axial position of the catheter base 162 relative to the deflection knob 156.

Pull cable 122 extends from the distal tip 118 of the steerable catheter past catheter base 162 and through deflection housing tube 150, and terminates at pull cable stop 168, with pull cable stop 168 fixed into position relative to deflection housing tube 150 by setscrew 169. It will be understood that slot 171 in pull cable stop 168 will permit attachment of setscrew 169 in several locations thereby enabling adjustment of the tension of pull cable 122 to effect the overall sensitivity of the deflection assembly. As best shown in FIG. 13A, pull cable 122 may pass through pull cable stop 168 through aperture 192 to be retained thereby, or will terminate at pull cable stop 168 by bond other means. Furthermore, center tube 114 will pass through pull cable stop 168 through aperture 194, as shown, or pull cable stop 168 can be positioned to one side of the proximal end of deflection housing 150 (not shown) for lateral clearance of center tube 114 therethrough. As deflection knob 156 is rotated in one direction towards the distal end of deflection housing tube 150, the distance between the axial position of the deflection knob 156 and the proximal end of the deflection housing tube 150 will be increased, resulting in increased tension in the pull cable 122, deflection of the flat shim 120 out of its own plane, and advance of the proximal outer jacket portion 126 relative to the pull cable 122. As the deflection knob 156 is rotated in the opposite direction, the distance between the axial position of the deflection knob 156 and the deflection housing tube 150 is decreased, thereby resulting in a corresponding decrease in tension of the pull cable 122 and a return to an un-deflected position. The deflection module may be used alone for applications requiring only deflection of the distal tip 118.

For applications such as TMR, fiber advance means module is removably coupled to the deflection module as shown in a preferred embodiment, by second one or more helical threads 181. It will be understood that the fiber advance mechanism can be coupled to the steerable catheter 100 of the present invention utilizing other coupling means, including varying pitch threaded systems, bayonet mount systems, adhesives, etc.

Referring now to FIGS. 1, 12, 14A and 14B, a "Tuohy-Borst" type compression adapter 170 for releasably coupling to a fiber optic bundle or other laser delivery means 116 (see FIG. 1) is located at the proximal end of the steerable catheter 100. Compression nut 173 tightens around laser delivery means 116 and retains it fixed therein. A depth-stop control nut 180, or other manually or otherwise controllable depth stop means, is provided distal to the adapter 170. Extension 182 extends proximally to terminate at luer fitting 185 and extends distally to advance slider 184 with fluid seal 188. Center tube 114, coupled to distal tip 118 and extending proximally, floats freely through catheter base 162, deflection housing tube 150 and through fluid seal 188, and terminates within extension 182.

Referring now to FIG. 12, depth stop control nut 180 can be positioned as desired on extension 182 so as to limit extension of laser delivery means 116. Thus, as control nut 180 is moved along extension 182, the maximum distance A can be traveled in precise increments, optionally by use of a calibrated depth scale 187 threaded over extension 182 and/or extending from nut 180. In the preferred embodiment used for TMR, such travel could be limited to between about 0 and about 3 centimeters, or more or less. Advance housing 172 has a slot 174 on one side for retaining thumb advance button 175 coupled to advance slider 184. Forward translation of thumb advance button 175, therefore, results in unison forward translation of adapter 170, depth control nut 180, extension 182, advance slider 184 and fluid seal 188 along with laser delivery means 116 (not shown), as permitted through distance A. Compression spring 176 or other biasing means maintains advance button 175 biased backward, in a proximally retracted position. As will be understood, immediately preceding operational advancement and/or operational retraction, as in retro-lasing which will be more fully explained in the following, of a laser delivery means 116, the spring 176-biased advance slider 184 will retract the distal end 128 of the laser delivery means 116 such as an optical fiber or fiber bundle back inside the deflectable end portion 106 so as to prevent injury to the patient during deformation of the deflectable end portion 106 for progressive operative placement of distal tip 118.

A saline flush, drug solution, visualization or other therapeutic agent containing fluid can be provided to the steerable catheter via one branched arm 190 of adapter 170. Saline solution, drug or such other fluid will fill adapter 170. Proximal fluid seal such as compression nut 173, or other sealing means, will create a seal around optical fiber or other laser delivery means 116. Such sealing means include o-rings, as shown, rubber diaphragms, other elastic member, etc. Saline or other fluid will be prevented from escaping past adapter 170 around laser delivery means 116. Furthermore, by maintaining the pressure of said flush or other fluids somewhat above that developed in the left ventricle, in the case of TMR, such will flow around laser delivery means 116, and through the passageway 115 through center tube 114, thus preventing back flow of blood from the left ventricle into the steerable catheter. Additionally, fluid seal 188, as described in the foregoing, prevents fluid flow or back flush around the proximal end 117 of center tube 114. In a preferred embodiment, it will be understood that any backflow preventer, check valve, blood seal, etc. with the necessary operative function and suitability can be employed elsewhere on the steerable catheter 100 and will be included within the scope of the present invention. Saline solution or other fluid can also be used to activate extension of the piercing means 206 and 214, as shown in FIGS. 8A–9B.

It will be understood, and therefore included within the scope of this invention, that the manually operated fiber optic or other laser delivery means advance mechanism can be replaced with a wide range of different mechanisms or devices, including indexed or ratcheted mechanisms, electric drives with electronic controllers, etc., automated advance and retract controllers, etc.

FIG. 15 is a representative isometric view of a drug delivery apparatus 196 coupled to the proximal end 104 of steerable catheter 100 of the present invention. As shown, other tools may be attached to the modular handle 102 of the steerable catheter 100 of the present invention for operation through the center tube 114 in addition to the drug delivery or dispensing apparatus 196. It will be understood, therefore, that such drug delivery or dispensing apparatus 196 can be manually or automatically activated, can be adjustable or programmable to dispense individual aliquots of a predetermined volume, at a predetermined or specified rate, as desired.

Preferred Method

Figure 16:
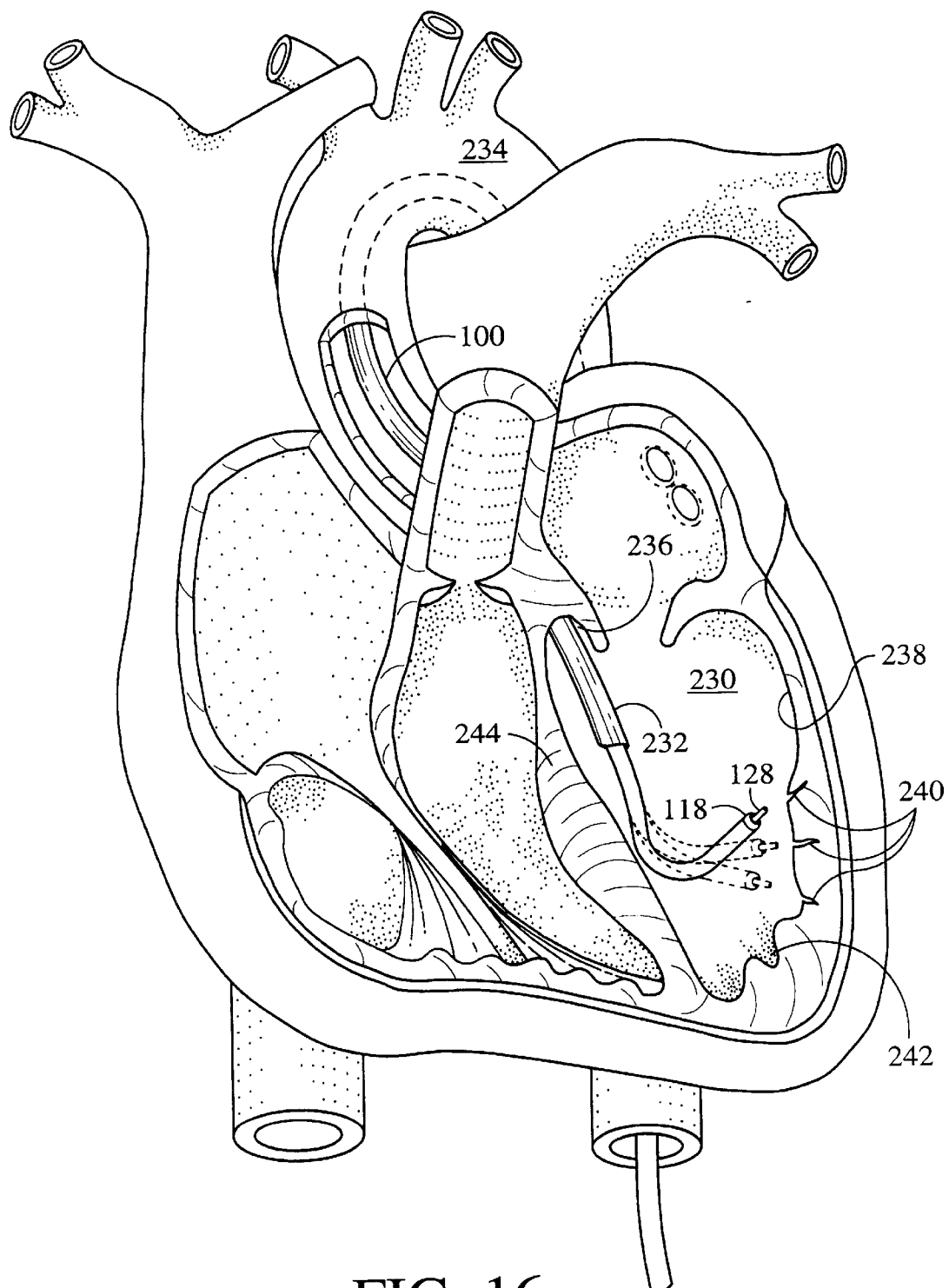
FIG. 16 is a representative perspective view of the steerable catheter of the present invention within the left ventricle.

FIG. 16 is a representative perspective view of the steerable catheter 100 of the present invention within the left ventricle 230. As indicated above with regard to FIGS. 1–15, the present invention is directed to "stand alone systems", in other words, to catheter systems which are guided into and through parts of the body, such as into the left ventricle, optionally without the use of a guide catheter 232 or other guide system. Such guide catheters are well known and may be used with the present invention, and therefore are included within the scope of this invention. Typically, entry into the vasculature is made through the femoral artery. If used, the physician steers an optional guide wire (not shown) into the left ventricle 230, and slides the guide catheter 232 over the guide wire, over the aortic arch 234 and across the aortic valve 236.

However, as a "stand alone system", the traditional guide wire or guide catheter 232 need not be used. The distal tip 118 and deflectable end portion 106 of the steerable catheter 100 is extended over the aortic arch 234 and prolapsed through the aortic valve 236 into the left ventricle 230. The steerable catheter 100 can be guided into a selected position adjacent a selected surface 238, in this case a portion of endocardium. Thus, by sequentially deflecting the deflectable end portion 106 of the steerable catheter 100 and/or by rotating the steerable catheter 100, extending the distal end 128 of a laser delivery means 116 or other functional device therethrough, delivering laser energy or performing other therapy, visualization or diagnostic, and retracting the distal end 128 of the laser delivery means 116 or other functional device back into the deflectable end portion 106, the steerable catheter 100 can treat a series of individual, selected treatment points 240 of endocardium. Such treatment points 240 would typically be TMR channels or stimulation sites. Another feature of the present invention is the ability to accurately position and stabilize the distal tip 118 of steerable catheter 100 in the apex 242 of the left ventricle 230 for treating therein.

Alternatively, retro-lasing can be performed. This novel method includes the steps of advancing the distal tip 128 of laser delivery means 116 a selected distance into the myocardium and then delivering laser energy to create a TMR channel or other treatment site while simultaneously retracting the fiber, laser delivery means 116 or other functional device. With this procedure, with regard to TMR especially, inasmuch as laser energy is only delivered during retraction of the fiber, the possibility of advancing the fiber too far and lasing through an epicardial surface is eliminated, and the risks of complications arising from such epicardial perforations, including but not limited to cardiac tamponade (a buildup of pressure in the pericardial sac caused by the presence of an excess of fluid such as blood), proliferation of adhesions between the epicardium and the pericardial sac (thereby preventing normal, frictionless enclosure of the heart muscle within the pericardial sac), etc. are minimized.

Furthermore, adjunct use of appropriate drug delivery apparatus, blood seal means, depth stop apparatus such as clamps, bushings, etc., visualization means, marker means as well as other hardware and methodology will be considered within the scope of the present invention. Additionally, use of electrophysiology (EP) readings from the distal tip 118 for confirming tissue contact will be particularly useful.

The present invention is intended for use with any medical laser. In particular, the Holmium or excimer laser is particularly suited to the present invention. However, any suitable laser source, pulsed or otherwise, could provide laser energy to the laser delivery means of the present invention for performing the method of the present invention. Likewise, the steerable catheter and surgical equipment, including laser delivery means, referred to in the present document as well as that known and used in medicine and other disciplines today and in the future, will be included in the scope of this disclosure. Such laser delivery means include, but are not limited to, individual optical fibers as well as bundles of fibers with and without piercing tips and with or without firing tips or fiber ends having shaped or contoured end faces for selectively diverging the laser beam or other laser energy diverging means, rods, mirrors configurations and other laser delivery means with and without focusing lens and the like. It will also be understood that the steerable catheter and method of the present invention as described herein including the novel combination or use with of any conventional mechanism or method which are known to those skilled in the art, are included within the scope of this invention. Furthermore, with regard to non-laser TMR, a cannula or trocar assembly may be extended into the tissue of the left ventricle, with or without use of a mechanical piercing tool.

It will further be understood that while the present invention has been described for performing TMR on endocardial surfaces in the left ventricle, the apparatus and methods described herein are equally intended for use in any suitable procedure, including but not limited to procedures where any device need be extended through a guide catheter to an opening or other point within the body for other medical procedures including laser treatment, visualization, biopsy, etc. "Stimulation", for example, is performed by using laser energy to create zones or pockets, optionally interconnected at least initially by small channels ablated through the tissue, for the introduction of blood born growth and healing factors and stimulated capillary growth surrounding the lased zones or pockets to create an increased supply of oxygen to the tissue and thus a revitalization of the heart muscle. Methods and apparatus for causing stimulation are more fully described in co-pending U.S. patent application Ser. No. 08/664,956 filed Jun. 13, 1996.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true spirit and scope of the invention.

We claim:

1. A method of forming revascularization channels or stimulation sites in myocardium from an endocardial layer within a left ventricle of a heart comprising:
   (a) providing a catheter having an outer jacket with a proximal end and a distal end with a deflection device therein coupled to a distal tip thereof, the catheter having an actuating assembly at the proximal end for activation of the deflection device and an inner tube movably mounted within the outer jacket, the inner tube having a proximal end and a distal end attached to the distal tip, the catheter further having a treatment tool slidably mounted within the inner tube and egressible from the distal tip of the jacket and a treatment tool advance mechanism attached to the handle and having an actuator;
   (b) advancing the catheter through vasculature into the left ventricle;
   (c) positioning the distal tip of the catheter at the endocardial layer;
   (d) operating the treatment tool advance mechanism to advance the treatment tool from the distal tip; and
   (e) operating the treatment tool to form a revascularization channel or stimulation site during advancement.

2. The method of claim 1 wherein the treatment tool is an optical fiber laser delivery device adapted for connection to a source of laser energy.

3. The method of claim 2 wherein step (c) further comprises activating the deflection device to deflect the distal tip.

4. The method of claim 2 wherein the catheter further comprises a piercing tool and the method further comprises the following step prior to step (d) piercing the endocardial layer with the piercing tool.

5. The method of claim 2 wherein the catheter further comprises a shape memory material and step (c) of the method further comprises activating the shape memory material to deflect the distal tip of the catheter during positioning.

6. The method of claim 2 further comprising, after step (e), the step of delivering a drug into the revascularization channel or stimulation site.

7. The method of claim 1 further comprising, prior to step (b), advancing a guide catheter through the vasculature into the left ventricle, and wherein step (b) further comprises advancing the catheter through the guide catheter into the left ventricle.

8. The method of claim 1 wherein the treatment tool is a drug delivery device.

* * * * *